United States Patent [19]
Hase et al.

[11] Patent Number: 5,849,487
[45] Date of Patent: Dec. 15, 1998

[54] NUCLEIC ACID DETECTION BY REPETITIVE SYNTHESIS AND DEGRADATION OF A NUCLEOTIDE ON A NUCLEASE RESISTANT OLIGONUCLEOTIDE

[75] Inventors: Tetsu Hase; Harumi Masubuchi, both of Otawara, Japan

[73] Assignees: Eiken Chemical Co., Ltd., Tokyo; Tanabe Seiyaku Co., Ltd., Osaka, both of Japan

[21] Appl. No.: 590,674

[22] Filed: Jan. 29, 1996

Related U.S. Application Data

[63] Continuation of Ser. No. 356,137, Dec. 15, 1994, abandoned.

[30] Foreign Application Priority Data

Dec. 28, 1993 [JP] Japan .................................. 5-337863

[51] Int. Cl.$^6$ .............................. C12Q 1/68; C12P 19/34; C07H 21/02
[52] U.S. Cl. ............................ 435/6; 435/91.1; 435/91.2; 435/91.52; 435/193; 435/194; 435/196; 536/24.3
[58] Field of Search .............................. 435/6, 91.1, 91.2, 435/91.21, 91.52, 194, 193, 196; 536/24.3, 24.31, 24.32, 24.33

[56] References Cited

U.S. PATENT DOCUMENTS

| | | | |
|---|---|---|---|
| 4,464,359 | 8/1984 | Suhadolnik et al. | 424/180 |
| 4,656,127 | 4/1987 | Mundy | 435/6 |
| 4,971,903 | 11/1990 | Hyman | 435/6 |
| 5,210,015 | 5/1993 | Gelfand et al. | 435/6 |
| 5,487,972 | 1/1996 | Gelfand et al. | 435/6 |

OTHER PUBLICATIONS

Hershfield et al, (1972), "Hydrolysis of template and newly synthesized deoxyribonucleic acid by the 3' to 5' exonuclease activity of the T4 Deoxyribonucleic acid polymerase" J. Biol. Chem. 247(11):3393–3404.

Tang et al, (Jun. 1993), "Self stabilized antisense oligodexynucleotide phosphorothioate properties and anti–HIV activity", Nucleic Acids Res. 21(11):2729–2735.

Stratagene catalog (1988), p. 39.

Kunkel et al,(1981), "Deoxynucleoside (1–thio) triphosphates prevent proofreading during in vitro DNA synthesis", Proc. Natl. Acad. Sci. 78(11):6734–6738.

Ott et al, (1987), "Protection of oligonucleotide primers against degradation by DNA polymerase I", Biochemistry 26:8237–8241.

Gupta et al, (1984), "The effect of the 3' 5' thiophosphoryl linkage on the exonuclease activities of T4 polymerase and the Klenow fragment", Nucleic Acids Res. 12(14):5897–5911.

Skerra, (1992), "Phosphorothioate primers improve the amplification of DNA sequences by DNA polymerases with proofreading activity", Nucleic Acids Res. 20(14):3551–3554.

*Primary Examiner*—Stephanie W. Zitomer
*Assistant Examiner*—Jeffrey Fredman
*Attorney, Agent, or Firm*—Fitzpatrick, Cella, Harper & Scinto

[57] ABSTRACT

The present invention relates to a method of detecting a polynucleotide, comprising hybridizing a polynucleotide of known nucleotide sequence with a nuclease-resistant oligonucleotide primer having a sequence complementary to a part of the polynucleotide, then adding at least one kind of deoxynucleoside triphosphate, DNA polymerase and nuclease thereto, synthesizing a complementary strand being a nucleotide species located adjacent to the 3'-terminal of the primer and complementary to the polynucleotide, followed by decomposition thereof, the synthesis and decomposition of the complementary strand being repeated one or more times, and detecting the resulting pyrophosphoric acid or deoxynucleoside monophosphate. The present invention also includes a detection kit used for this method of detecting a polynucleotide.

7 Claims, 7 Drawing Sheets

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Synthetic DNA"

( v i ) ORIGINAL SOURCE:

-continued (A) ORGANISM: cytomegalovirus (CMV)

(x i) SEQUENCE DESCRIPTION: SEQ ID NO:1:

CCCCGAAATG GGACCCAGTA CGGAT
25

(2) INFORMATION FOR SEQ ID NO:2:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "Synthetic DNA"

(v i) ORIGINAL SOURCE:
        (A) ORGANISM: Human oncogene Ki- ras/12

(x i) SEQUENCE DESCRIPTION: SEQ ID NO:2:

ATAAACTTGT GGTAGTTGGA GCTG
24

(2) INFORMATION FOR SEQ ID NO:3:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "Synthetic DNA"

(v i) ORIGINAL SOURCE:
        (A) ORGANISM: HBV-e antigen gene in HBV-DNA (x i) SEQUENCE DESCRIPTION: SEQ ID NO:3:

AATGCCCCTA TCTTATCAAC ACTTC
25

NUCLEIC ACID DETECTION BY REPETITIVE SYNTHESIS AND DEGRADATION OF A NUCLEOTIDE ON A NUCLEASE RESISTANT OLIGONUCLEOTIDE

This application is a continuation of application Ser. No. 08/356,137, filed Dec. 15, 1994now abandoned.

BACKGROUND OF THE INVENTION

1. Field of the Invention

The present invention relates to a method of detecting a polynucleotide containing a specific sequence present in a sample (hereinafter referred to as "target polynucleotide") useful for the diagnosis of genetic disorders and infectious diseases. A kit for detecting a polynucleotide used for said method is also included.

2. Description of the Prior Art

A method of analysis based on the complementarity between nucleotide sequences enables the direct analysis of genetic characters. Hence, this is a very powerful means for the identification of genetic disorders, a carcinomatous change of normal cells, microorganisms, etc. Because it detects the gene directly, time-consuming and troublesome operations such as cultivation etc. may be eliminated.

However, it is generally not easy to detect a trace amount of target nucleotide in a sample, so the target nucleotide itself or a signal thereof should be amplified. As a method of amplifying the target nucleotide, the PCR (Polymerase Chain Reaction) process is known. The PCR is the most conventional method as an in vitro technique for amplification of nucleic acid. However, the PCR presents known disadvantages such as the requirement for a temperature control unit in practice, inadequate quantification due to logarithmic amplification, and is easily affected by contamination.

That is, a reaction e.g. PCR in which DNA is amplified several million times may easily lead to erroneous results brought about by simultaneous amplification of trace amounts of contaminated DNA. This causes a serious problem particularly when a large number of samples are to be simultaneously dealt with. Hence, a laboratory is divided, etc. for preventing such contamination. Further, there is a chemical approach in which a uracil base is incorporated during PCR and then the sample is treated with uracil-glycosylase before another PCR amplification begins, so that only an amplification product from other reaction system originating in a contaminated sample is decomposed. However, these prior approaches are not always satisfactory for preventing contamination.

As a method of amplifying a signal, a method of amplifying signal RNA by Qβ replicase is known (P. M. Lizardi et al., Bio/Technology, 6, 1197–1202 (1988)). However, since this method requires an amplification sequence to be inserted into a sequence capable of recognition by the replicase, the sequence inserted and the position into which it is inserted are stereostructurally limited. This amplification method also presents the problem of contamination, similar to the PCR.

Besides the above amplification of the target nucleotide sequence, there are signal amplification methods which detect decomposition products.

For example, EP-0455517/A1 discloses a signal amplification method comprising hybridizing an oligonucleotide probe DNA with the target nucleotide, treating it with a restriction enzyme, and detecting the cleaved probe fragment. Although its detection sensitivity is lower than the PCR, this method can be practiced with excellent quantification without requiring any special equipment. In the method, however, a second specific oligonucleotide is required with the probe DNA to permit the reaction to repeatedly occur. Another disadvantage lies in the limitation of the specific site for restriction enzymes.

A cycling assay by λ-exonuclease that specifically cleaves double-stranded DNA has also been developed (C. G. Copley et al., BioTechniques, Vol. 13, No. 6, 882–892 (1992)). This method comprises hybridizing an oligonucleotide probe with a sequence complementary thereto, allowing λ-exonuclease to act on the formed double-stranded DNA to decompose the hybridized probe DNA. The probe DNA is replaced by another probe DNA which is then decomposed. This cycling reaction repeats. In this method, the presence of a specific DNA sequence can be estimated by detecting the decomposed probe. This method is advantageous over methods using restriction enzyme (EP-0455517/A1) in that the reaction principle is simple and the restriction site is not required.

However, λ-exonuclease requires a probe DNA phosphorylated at the 5'-terminal as the substrate. A problem of this method seems to be the difficulty of reproduction of the 5'-phosphorylated probe. When the probe DNA is chemically synthesized in DNA synthesizer, the 5'-terminal is not phosphorylated. Therefore, it is difficult to confirm the 5'-terminals are phosphorylated completely. Another problem is the low turn over number of cycling reactions (about 500 times/hour according to the literature) because hybridization between the probe DNA and template DNA, which occurs repeatedly in the cycling assay, and seems to take reaction time, is rate-determining at a constant temperature.

Another cycling assay by an exonuclease is disclosed in EP-500224/A1. In this method, the synthesis of a complementary strand from a primer proceeds simultaneously with the decomposition of the same primer from the other side by a 5'→3' exonuclease so that another primer hybridizes with the target sequence in place of the decomposed primer hybridized before. In this way, one cycle reaction, i.e. the synthesis of a complementary strand by DNA polymerase and the degradation of the synthesized strand, repeatedly proceeds. Although complex temperature control such as in the PCR is not required in the above process, turn over number (the number of times hybridization between primer and target nucleotide occurs) is still low since the hybridization step must be repeatedly carried out.

To solve the above problems, the present inventors have developed a method of detecting a nucleotide sequence in which enhancing reagent is used along with exonuclease III (Japanese Laid-Open Patent Publication No. 327499/94). This method is excellent in that the probe can be easily prepared, no special temperature control equipment is required, and is free from contamination. Even though the enhancing reagent raises the turn over number, high sensitivity cannot necessarily be obtained, since the probe DNA is hard to repeatedly hybridize.

In the amplification methods described heretofore, an oligonucleotide added as the primer turns into an amplified product and does not function as the primer anymore. So the oligonucleotide should be added in large excess relative to the estimated amount of the target nucleotide. An extremely large amount of oligonucleotide should previously be added particularly in a system such as the PCR which performs amplification in logarithmic form. A smaller amount of oligonucleotide is preferable from the economical viewpoint whether it is chemically synthesized or obtained from biological materials.

OBJECTS AND SUMMARY OF THE INVENTION

Hence, an object of the present invention is to provide a method of detecting a polynucleotide, which is less susceptible to the influence of contamination in a simple reaction system without requiring any special equipment like complex temperature control. Another object of the present invention is to provide a detection method applicable to a wide variety of nucleotide sequences which are not limited. Still another object of the present invention is to provide a detection method in which higher sensitivity and quantification can be achieved depending on suitable selection of the present detection system.

As a result of their eager research, the present inventors successfully developed a method in which a nuclease acting on a double-stranded DNA but not acting on a single-stranded DNA is used together with DNA polymerase so that the signal can be amplified.

That is, the present invention encompasses:

1. A method of detecting a polynucleotide, comprising hybridizing a polynucleotide of known nucleotide sequence with a nuclease-resistant oligonucleotide primer having a sequence complementary to a part of said polynucleotide, then adding at least one kind of deoxynucleoside triphosphate, DNA polymerase and nuclease thereto, synthesizing a complementary strand being a nucleotide species located adjacent to the 3'-terminal of said primer and complementary to said polynucleotide, followed by decomposition thereof, the synthesis and decomposition of said complementary strand being repeated one or more times, and detecting the resulting pyrophosphoric acid or deoxynucleoside monophosphate.

2. A method of detecting a polynucleotide according to item 1, wherein the oligonucleotide primer is phosphorothioated at the 3'-terminal region.

3. A method of detecting a polynucleotide according to item 1 or 2, wherein the DNA polymerase is selected from the group consisting of DNA polymerase I, the Klenow fragment of DNA polymerase I, T4 DNA polymerase, T7 DNA polymerase and Phi29 DNA polymerase.

4. A method of detecting a polynucleotide according to any one of items 1 to 3, wherein the nuclease is exonuclease III.

5. A method of detecting a polynucleotide according to any one of items 1 to 4, wherein an atom or a molecule other than phosphoric acid molecules at β- and γ-positions of deoxynucleoside triphosphate is labeled with a radioisotope, and the deoxynucleoside monophosphate formed by nuclease reaction is detected.

6. A method of detecting a polynucleotide according to any one of items 1 to 4, wherein the deoxynucleoside monophosphate formed by nuclease reaction is separated by chromatography and optically measured.

7. A method of detecting a polynucleotide according to any one of items 1 to 4, wherein the pyrophosphoric acid which is formed upon incorporation of a complementary base by DNA polymerase is allowed to react with adenosine-5'-phosphosulfate and adenosine triphosphate sulfurylase to form adenosine triphosphate which is then detected.

8. A method of detecting a polynucleotide according to item 7, wherein adenosine triphosphate is measured by luciferin-luciferase reaction.

9. A kit used in the method of detecting a polynucleotide according to any one of items 1 to 8, comprising:
  1. a nuclease-resistant oligonucleotide primer having a sequence complementary to a part of the target polynucleotide of known nucleotide sequence;
  2. a DNA polymerase;
  3. at least one kind of deoxynucleoside triphosphate; and
  4. a nuclease with the activity of decomposing a double-stranded DNA in the 3'→5' direction.

10. A kit for detecting a polynucleotide according to item 9, further comprising reagents for detecting deoxynucleoside monophosphate.

11. A kit for detecting a polynucleotide according to item 9, further comprising reagents for detecting pyrophosphoric acid.

Hereinafter, the present invention is described in detail.
(A) The detection target in the present invention is a polynucleotide of known nucleotide sequence.

The target polynucleotide of the present invention includes, but is not limited to, those derived from organisms such as animal, plant, bacterium, yeast, mold fungi, mycoplasma, rickettsia, virus, etc. The type of polynucleotide includes, but is not limited to, genomic nucleic acid and RNA virus- or mRNA-derived cDNA.

A DNA sequence other than the target polynucleotide or a sequence as a potential primer for DNA synthesis can be a problem for analysis in practice. There is a possibility of the contamination of the sample with DNA polymerase- or nuclease-inhibiting substances and deoxynucleoside triphosphate. Further, in cases where pyrophosphoric acid is used as the signal from the target nucleotide, the pyrophosphoric acid in a sample can interfere with the analysis.

Hence, the minimization of such contamination is preferred for amplification in the present invention. The present invention can provide a background-free, highly sensitive detection system, for example by capturing the target nucleotide with a solid phase-bound capture probe etc. and washing it. If the capture probe is bound at the 5'-terminal to a solid phase (H. Kohsaka et al., Eur. J. Immunol., 23, 1895–1901 (1993); H. Kohsaka et al., Nucleic Acids Research, 21, 3469–3472 (1993)), the capture probe itself can also be used as the primer for application of the present experimental method. The above-mentioned pyrophosphoric acid in the sample can also be removed enzymatically by pyrophosphatase.

In a preferable embodiment of the present invention in which particularly one nucleotide is repeatedly incorporated and decomposed, a point mutation can be detected as described below.

The method of detecting a point mutation is known as described in e.g. EP-123513/A1. This method is based on the reaction principle that in synthesis of a complementary strand following a primer DNA, a nucleotide derivative which contains nuclease resistance is incorporated if a point mutation is present (or absent). Because the reaction product becomes exonuclease resistant once the nucleotide derivative is incorporated, the point mutation can be detected by examination of the presence of the decomposition of the nucleotide by nuclease.

The above method agrees with the present invention in some elements. However, an essential difference lies in that, as the indicator of the presence of point mutation, the above method uses the presence or absence of nuclease resistance fragment, whereas the present invention uses the occurrence of repeatedly proceeding reaction. Further, the sensitivity of the present method in the detection of point mutations is superior to that of the above method.

(B) The present invention is characterized by hybridizing a known polynucleotide with a nuclease-resistant oligonucleotide primer having a sequence complementary to a part of said known polynucleotide.

In the present invention, the term "complementary" refers to the state permitting two nucleic acid chains to form a double-stranded chain via hydrogen bonding according to the Watson-Crick base-pairing. More specifically, thymine (T) is complementary to adenine (A), and cytosine (C) to guanine (G). In the present invention, it is not required for the primer to be absolutely complementary to the target polynucleotide sequence insofar as the target oligonucleotide as a whole can hybridize with the target polynucleotide. More specifically, at least 70% of the primer oligonucleotide should be complementary to the target polynucleotide on condition that the 3'-terminal of the primer hybridizes and is completely complementary to the target nucleotide. Less than 70% complementarity is not preferable owing to insufficient hybridization. In the present invention, the condition that the 3'-terminal of the oligonucleotide primer is complementary to the target nucleotide to which the primer hybridized is a requisite for the nucleotide elongation at the 3'-terminal. If the 3'-terminal region is not able to hybridize with the target DNA and remains single-stranded, the primer region cannot be recognized by polymerase and nuclease.

The oligonucleotide primer in the present invention is characterized by being complementary to "a part" of a known polynucleotide as the target. This is because the present method is characterized by detecting a specific kind of deoxynucleotide which is added to the reaction system and then bound by DNA polymerase to the 3'-terminal of the oligonucleotide primer. That is, if the target polynucleotide, which serves as the template for the substrate deoxynucleotide to be bound to the 3'-terminal of the primer, is not known, no one can know what kind of deoxynucleotide should be added to the system as the substrate. Hence, it is required for the oligonucleotide primer to be complementary to "a part" of known target polynucleotide.

The oligonucleotide primer used in the present invention should be nuclease-resistant to prevent decomposition by the nuclease present in the system.

The method of conferring nuclease resistance on the oligonucleotide primer is not particularly limited, and any method known to the art may be used.

For example, an oligonucleotide primer with nuclease resistance can be synthesized in a DNA synthesizer by introducing a phosphorothioate bond into the target site of the primer in a method known to the art. More specifically, the oligonucleotide primer is synthesized in e.g. the solid phase phosphoramidite method in which the conventional oxidation step by iodine water is replaced by an oxidation treatment with a suitable reagent for phosphorothioation, whereby a phosphorothioate bond can be introduced in place of a phosphodiester bond. As the phosphorothioation reagent, mention may be made of 3H-1,2-benzodithiole-3-one 1,1-dioxide (Beaucage's Reagent), TETD/acetonitrile (TETD: tetraethylthiuram disulfide), etc. This method enables introduction of a phosphorothioate bond into the oligonucleotide at an arbitrary site.

As an alternative method of introducing a phosphorothioate bond into the oligonucleotide primer, the enzymatic DNA synthesis using DNA polymerase may be carried out in the presence of deoxyribonucleoside triphosphate in which an oxygen atom at the α-position is replaced by sulfur. As such substituted compounds, mention may be made of α-S-deoxythymidine triphosphate, α-S-deoxycytosine triphosphate, α-S-deoxyadenine triphosphate and α-S-deoxyguanine triphosphate (which all are collectively referred to hereinafter as SdXTP). DNA polymerase incorporates SdXTP in place of deoxynucleoside triphosphate (hereinafter referred to as dXTP) to give a phosphorothioated oligonucleotide primer containing nuclease resistance. A phosphorothioate bond can also be introduced by DNA polymerase into an oligonucleotide hybridized with the target polynucleotide. That is, the oligonucleotide primer is given nuclease resistance at the time of the analysis, and thus it may not necessarily be prepared beforehand.

In this case, DNA polymerase elongates at least 2 nucleotides, i.e. at first SdXTP is incorporated and subsequent dXTP is bound next to the incorporated SdXMP (α-S-deoxynucleoside monophosphate). The latter dXMP is subject to the action of nuclease. Once nuclease resistance is given, the subsequent reaction can proceed according to the reaction principle described below.

In any case, the presence of a phosphorothioate bond in place of a phosphodiester bond in the vicinity of the 3'-terminal of the primer confers on the oligonucleotide primer resistance to nuclease attacking the 3'-terminal side. However, it is noted that hybridization efficiency is decreased with increased nuclease resistance by introducing more phosphorothioate bonds to the whole of the oligonucleotide primer. In consideration of the balance between hybridization efficiency and nuclease resistance, one or a few phosphorothioate bonds are preferably used. Sufficient nuclease resistance is given by introducing only one phosphorothioate bond. However, more perfect nuclease resistance is given by introducing a few phosphorothioate bonds, preferably three phosphorothioate bonds.

As compared with dxTP, the incorporation efficiency of SdXTP by DNA polymerase is relatively low. Hence, SdXTP should be added before addition of dXTP, or its excess addition may be required.

Besides the above-mentioned phosphorothioation, methylphosphonate bond, phosphoroamidate bond, polyamide nucleic acid (PNA) bond, etc., can be applied as the means of conferring nuclease resistance. These bonds modify the nucleotide at the phosphoric acid binding site, ribose site and base site or in the structure thereof to give nuclease resistance.

Alternatively, an RNA can be used as the oligonucleotide primer. RNA is substantially resistant to a DNA-acting nuclease. Hence, the use of RNA primer eliminates the need for modified oligonucleotide primer resistant to a DNA-acting nuclease. However, since some members of DNA-acting nuclease and DNA polymerase possess RNase H activity, too, it is noted that such enzymes decompose RNA primer to deteriorate sensitivity.

In the present invention, the number of the nucleotides in the oligonucleotide primer is at least 6, preferably 10 to 50, more preferably 15 to 30.

Given a primer of less than 6 nucleotides, hybridization is hard to occur under normal conditions. And even if the short oligomer hybridizes the target DNA, non-specific reactions will occur at high efficiency. On the other hand, if an oligonucleotide primer is given nuclease resistance by phosphorothioation, its affinity for template (Tm) becomes low, so a certain length is required for compensating for a decrease in affinity. However, a primer of more than 30 nucleotides is unfavorable from the economical viewpoint, because as the primer strand is elongated, the yield in chemical synthesis is lowered. In addition, given a too long primer, non-specific reaction easily occurs, because a double-stranded chain via hydrogen bonds can be readily formed intramolecularly or between primers. Hence, a too long primer causes non-specific synthesis etc., and is thus not preferred.

Some kinds of DNA polymerase such as DNA polymerase I possess a 5'→3' exonuclease activity which digests double-stranded DNA. For use of this kind of enzyme as DNA polymerase, it is preferred to make the primer nuclease-resistant at the 5'-terminal in order to prevent decomposition from the 5'-terminal region. DNA polymerases, such as the Klenow fragment and Phi29 DNA polymerase, are preferred because they are free of such activity, and thus no particular modification of the 5'-terminal is required.

In a conventional method of amplifying a nucleotide sequence, the oligonucleotide primer itself is consumed to form an amplified product. Therefore, the oligonucleotide primer is added in excess relative to the target DNA to be detected. This in contrast to the present invention because once hybridized the oligonucleotide primer can repeatedly function so as to permit the reaction to proceed quantitatively in an at least equimolar amount relative to the template nucleotide sequence. In practice, a sufficient amount of the oligonucleotide primer is preferably used for attaining hybridization-favoring equilibrium. Although the estimation of the content of the target sequence before analysis may be difficult, high sensitivity can be secured by the presence of an oligonucleotide primer which is at least equimolar and preferably 5-fold excess relative to the intended range of detection.

Conditions for hybridization are not particularly limited insofar as the subsequent reaction can proceed in the presence of DNA polymerase and nuclease. Hence, the reaction conditions should be selected so as to maintain and to optimize the nuclease activity when the thermostability of nuclease is not so high like Taq polymerase used in the PCR. Other factors such as buffer, pH, etc., should also be selected so as to achieve sufficient nuclease activity and sufficient hybridization. More specifically, the temperature is in the range of 20° to 55° C., preferably 30° to 45° C., and the pH value is in the range of about 7 to 9, preferably pH 7.5 to 8.5, in e.g. Tris-HCl buffer.

As shown in the Examples, a sample is heated at 100° C. for 5 min. in order to denature the target DNA in a solution composed exclusively of 0.1 pmol primer, 50 mM Tris-HCl buffer (pH 7.5) and 10 mM MgCl$_2$ and subjected to annealing at 65° C. for 10 min., and the annealing may immediately be followed by treatment at 37° C. with DNA polymerase and nuclease.

If the pyrophosphoric acid accumulated in the reaction is enzymatically determined, conditions such as pH, salt concentration, temperature, etc., should be suitably selected so as to be adapted to the enzyme reaction.

Stabilizers for DNA polymerase or nuclease may be added. Examples of stabilizers are bovine serum albumin (BSA), dithiothreitol (DTT) and β-mercaptoethanol, which are added in an amount of 10 to 500 µg/ml for BSA, about 1 mM for DTT, and about 10 mM for β-mercaptoethanol.

When the target polynucleotide is double-stranded, it should be previously made single-stranded by denaturation. Denaturation may be effected in any method known to the art, such as heat denaturation, acid denaturation, alkali denaturation, etc., among which heat denaturation (heating at 90°–100° C. for 5 min. or more) is preferred for the simple procedure and reliability.

Before addition of DNA polymerase, the sample may be treated with exonuclease whereby a hybridization of DNA other than target DNA and non-specific reaction caused by non-specific hybridization can be prevented.

(C) The present invention is characterized in that after the above hybridization, at least one kind of deoxynucleoside triphosphate, DNA polymerase and nuclease are added to the system so that a nucleotide located adjacent to the 3'-terminal of said primer and complementary to the target polynucleotide is incorporated, followed by decomposition thereof, the synthesis and decomposition of the complementary strand being repeated one or more times.

The reaction principle of the present invention is illustrated in FIG. 1 and Scheme 1.

(Scheme 1)

There occurs hybridization with the oligonucleotide primer (which is made nuclease-resistant by the presence of a phosphorothioate bond between the T-C at the 3'-terminal):

(target single-stranded DNA) 5'- . . . CCGGAAGTGT-TGATAAGATAGGGGCATTAGG . . . CTTCACAAC-TATTCTATCCCCGTA -5'(SEQ ID No:3)

(oligonucleotide primer)

↓

One molecule of PPi is formed upon elongation of C (designated *) at the 3'-terminal of the primer by DNA polymerase:

5'- . . . CCGGAAGTGTTGATAAGATAGGGGCATT-AGG . . . CCTTCACAACTATTCTATCCCCGTA -5'(SEQ ID No:3)

* ↓

PPi formation

C is cleaved off by nuclease to give dCMP:

5'- . . . CCGGAAGTGTTGATAAGATAGGGGCATT-AGG . . . CTTCACAACTATTCTATCCCCGTA -5'(SEQ ID No:3)

* ↓ decomposition product (dCMP)

↓

Another C is added to the 3'-terminal of the primer by DNA polymerase:

5'- . . . CCGGAAGTGTTGATAAGATAGGGGCATT-AGG . . . CCTTCACAACTATTCTATCCCCGTA -5'(SEQ ID No:3)

* ↓

PPi formation

↓ repetition

First, a oligonucleotide primer is hybridized with the target nucleotide. Then, a complementary strand is elongated by incorporation of one molecule of dXTP to the 3'-terminal of the oligonucleotide primer, simultaneously releasing one molecule of pyrophosphoric acid (PPi). Then the complementary strand is decomposed from the 3'-terminal by nuclease and one molecule of deoxynucleoside monophosphate (dXMP) release. Due to the site with nuclease resistance, the oligonucleotide primer itself is not decomposed by nuclease. It remains an intact nucleotide sequence and enables another round of elongation therefrom by DNA polymerase. The reaction repeats so that pyrophosphoric acid, and deoxynucleoside monophosphate formed by nuclease, are accumulated in the system.

At the time of the above reaction, the oligonucleotide primer can be made nuclease-resistant using the DNA polymerase reaction as described earlier.

The pyrophosphoric acid, or the deoxynucleoside monophosphate formed in decomposition by the nuclease, is used for the detection or quantification of the target nucleotide.

Further, the present detection method can constitute a system of detecting a target nucleotide having a point mutation if the site of the point mutation is previously known. That is, a sequence complementary to the region adjacent to the 5'-terminal of the point mutation is used as the oligonucleotide primer. When only one kind of dXTP corresponding to the nucleotide in the normal sequence is added as the substrate, no elongation occurs in the site of point mutation, and the reaction does not proceed. In this manner, the presence of the point mutation can be easily confirmed
(Scheme 2)

First, the oligonucleotide primer (which is made nuclease-resistant by the presence of a phosphorothioate bond between the T-C at the 3'-terminal) is hybridized:

target single-stranded DNA
5'- . . . CCGGAAGTGTTGATAAGATAGGGGCATT-AGG . . . CTTCACAACTATTCTATCCCCGTA - 5'(SEQ ID No:3)
oligonucleotide primer
↓

If the target is normal (G residue in this case), C (designated *) is elongated at the 3'-terminal of the primer by DNA polymerase:

5'- . . . CCGGAAGTGTTGATAAGATAGGGGCATT-AGG . . . CCTTCACAACTATTCTATCCCCGTA - 5'(SEQ ID No:3)
*

If G is replaced in point mutation by another nucleotide (e.g. A), no DNA elongation of T being complementary to A occurs in the presence of dCTP as the only substrate:

5'- . . . CCAGAAGTGTTGATAAGATAGGGGCATT-AGG . . . CTTCACAACTATTCTATCCCCGTA - 5'(SEQ ID No:3)
*

Even if a mutation is present within the region to be hybridized with the oligonucleotide primer, the presence of the point mutation can also be detected because the primer does not hybridize the target nucleotide and the reaction does not proceed.

The DNA polymerase used above catalyzes the elongation of a complementary strand in the 5'→3' direction from the oligonucleotide primer which has hybridized with the target nucleotide. Every known DNA polymerase so far possesses the activity of synthesizing DNA in the 5'→3' direction. No DNA synthesis occurs in the absence of a primer hybridized with a template strand. Hence, the present invention is based on high specificity depending on the hybridization between the primer and the template strand. As the DNA polymerase used in the present invention, mention may be made of DNA polymerase I, the Klenow fragment of DNA polymerase I, T4 DNA polymerase, T7 DNA polymerase, and Phi29 DNA polymerase, or mutations thereof.

When a DNA polymerase with a strong 3'→5' exonuclease activity such as T4 DNA polymerase or T7 DNA polymerase is used, it is possible to cut down the content of a nuclease, and in some cases it may even eliminate the use of the nuclease entirely. However, such a DNA polymerase may impair sensitivity since the enzyme can decompose phosphorothioate bonds to some extent. In this case, it is preferred to introduce several phosphorothioate bonds into the vicinity of the terminal of the primer or modify the primer by other means than phosphorothioation in order to make the primer more resistant to nuclease.

The nuclease used above is the one decomposing a double-stranded DNA in the 3'→5' direction. Exonuclease III is known as such a nuclease. Although exonuclease III derived from E. Coli is commercially available, it is possible to use any kind of exonuclease derived from other microorganisms or obtained by genetic recombination. Exonuclease III is used under almost the same conditions for DNA polymerases such as DNA polymerase I, its Klenow fragment, T4 DNA polymerase, etc., so the same reaction buffer can be used for both exonuclease III and DNA polymerase. Exonuclease III is highly preferred in the present cycling reaction because it decomposes specifically double-stranded DNA in the 3'→5' direction, does not decompose single-stranded DNA such as the target nucleotide and primer itself, and a primer is easily made to be exonuclease III-resistant by phosphorothioation or synthesized in the presence of SdXTP.

Deoxynucleoside triphosphate (dXTP) is used as the substrate to elongate DNA from the oligonucleotide primer by DNA polymerase. In the present invention, a polynucleotide of known sequence can be detected by analysis of one base elongation. Hence, the present reaction can proceed in the presence of one kind of deoxynucleoside triphosphate as the substrate corresponding to the target sequence. The substrate (dXTP) is added in a sufficient or excess amount relative to the mole number of the target nucleotide. Since it is usually difficult to exactly predict the amount of the target nucleotide before analysis, it is preferred to add at least 0.1 $\mu$M, preferably 1 $\mu$M or more to practically prevent the deficiency of the substrate (dXTP).

(D) The present invention is characterized by detecting pyrophosphoric acid or deoxynucleoside monophosphate.
① Detection of accumulated deoxynucleoside monophosphate In the present method, the target polynucleotide can be detected by measuring the deoxynucleoside monophosphate (dXMP) accumulated by decomposition of the incorporated nucleotide after polymerization.

To measure the dXMP, the substrate dXTP is labeled with a radioisotope ($^{32}$P or $^{33}$P) on a phosphorus atom at the $\alpha$-position; with $^3$H on a hydrogen atom in phosphoric acid at the $\alpha$-position, the deoxyribose moiety, or the base moiety; or with $^{14}$C on a carbon atom of the deoxyribose moiety. Then, the dXMP is separated from the substrate dXTP using a chromatographic techniques such as ion-exchange resin under monitoring the radioactivity, so that the dXMP is determined by its radioactivity. As the dXTP labeled with $^{32}$P on a phosphorus atom at the $\alpha$-position, dATP, dCTP, dGTP and dTTP are commercially available. As the dXTP labeled with $^{33}$P on a phosphorus atom at the $\alpha$-position, dATP and dCTP are also commercially available. And as the dXTP labeled with $^3$H on the base moiety, dATP, dCTP, dGTP and dTTP are commercially available.

Radiolabeled dXMP can be easily and qualitatively detected by measuring its radioactivity in autoradiography after separation by thin layer chromatography on ion exchange resin. As shown in the Examples, dXMP can also be quantitatively determined by counting the radioactivity of a cut spot piece in a scintillation counter. However, the labeling of a substrate with an isotope is not necessarily required for the separation and determination of dXMP. For example, after development of the reaction solution by thin layer chromatography coated with a commercial fluorescent pigment, dXMP can be visualized as a non-fluorescent spot upon exposure to ultraviolet light since the nucleotide absorbs ultraviolet light. Also, dXMP can be quantitatively detected by separating it by liquid chromatography and measuring its ultraviolet light absorption.
② Quantification of pyrophosphoric acid formed upon strand elongation by DNA polymerase In the present invention, the target polynucleotide can be detected by measuring the PPi formed upon elongation of dXMP by DNA polymerase.

The PPi can be enzymatically determined without any separation from dXMP and dXTP by chromatography etc. For example, the following known reaction 1 promises highly sensitive measurement in simple operation in a homogeneous system (T. Tabary et al., J. Immunological Methods, 156, 55–60 (1992)).
Reaction 1.
ATP sulfurylase PPi+adenosine-5'-phosphosulfate ---→ATP+S0$_4^{2-}$ luciferase ATP+luciferin+O$_2$---→AMP+PPi+oxyluciferin+CO$_2$ luminescence As another method of measuring pyrophosphoric acid, mention may be made of Anal. Biochem., 94, 117–120 (1979).

(E). EXAMPLE

The reaction system of the present invention is illustrated by referring to a specific oligonucleotide in the following reaction system (Scheme 3).
(Scheme 3)
A sequence specific to human cytomegalovirus (hereinafter referred to as CMV) in D fragment in the genome

5'-TTGTCCCGAA ATGAT→ATCCG TACTGGGTCC CATTTCGGGG←CACGTGCTGA-3'

5'-TTGTCCCGAA ATGATATCCG TACTGGGTCC CATTTCGGGG CACGTGCTGA CMV TAGGC ATGACCAGG GTAAAGCCCC -5'(SEQ ID No:1)
primer
↓

PPi is formed by elongation of A (designated *) by DNA polymerase

5'-TTGTCCCGAA ATGATATCCG TACTGGGTCC CATTTCGGGG CACGTGCTGA CMV ATAGGC ATGACCAGG GTAAAGCCCC -5'(SEQ ID No: 1)
primer
*+PPi
↓

Nuclease degrades the 3' bond consisting of T and A, and detaches dAMP. Then the position * becomes unoccupied and available for new incorporation of dAMP:
↓

5'-TTGTCCCGAA ATGATATCCG TACTGGGTCC CATTTCGGGG CACGTGCTGA CMV *TAGGC ATGACCAGG GTAAAGCCCC -5'(SEQ ID No: 1) primer
↓

Another A is elongated by DNA polymerase:

5'-TTGTCCCGAA ATGATATCCG TACTGGGTCC CATTTCGGGG CACGTGCTGA CMV ATAGGC ATGACCAGG GTAAAGCCCC-5'(SEQ ID No: 1) primer
*
↓ repeat the reactions

① In the detection of CMV, the primer sequence is derived from the D fragment in a restriction enzyme EcoRI fragment in genomic DNA.
The sequence is shown in Scheme 3.
In the following description, a complementary strand to the target sequence between "→" and "←" is used as the primer sequence (SEQ ID No: 1), although the primer sequence to be hybridized is not particularly limited, and any portion on the target sequence in Scheme 3 may be used. The bond between the A-T at the 3'-terminal of the primer is a phosphorothioate bond instead of a natural phosphodiester bond.

The presence of CMV sequence can be known by detection of the PPi or the decomposition product dAMP.

② A preferable method of the present invention, in which particularly one nucleotide is repeatedly incorporated and detached, can be used for the detection of point mutations as described above. In the following example, the point mutation of human oncogene Ki-ras/12 is detected. A known mutant of Ki-ras/12 is set forth in Scheme 4 (dots are assigned to the normal sequence).
(Scheme 4)
|→primer←|
normal sequence: 5'- AATATAAACT TGTGGTAGTT GGAGCTGGTG GCGTAGGCAA TTATATTTGA ACACCATCAA CCTCGACCAC CGCATCCGTT (SEQ ID No: 2)
mutant: 5'-............................T.............
...........................A............

The partial sequence (SEQ ID: 2) in Scheme 4 is used as the primer. The primer is made nuclease-resistant by the presence of a phosphorothioate bond between the T-G at the 3'-terminal. Only one kind of substrate, dGTP, is added for the reaction of DNA polymerase. In this example, dGTP should be incorporated if the sample has a normal sequence, and PPi and dGMP should be accumulated. When the sample has a mutation sequence, no complementary strand synthesis occurs in the absence of dTTP because the mutated sequence has an A residue. The presence of the point mutation can be confirmed if the reaction is initiated by addition of dTTP as the substrate. In this way, a point mutation can be detected in the present invention (see Scheme 5).
(Scheme 5)
dGTP is incorporated into the normal sequence.
dGTP
↓
ATAAACT TGTGGTAGTT GGAGCTG 3'(SEQ ID No:2) TTATATTTGA ACACCATCAA CCTCGAC-CAC CGCATCCGTT Schemes 4 and 5 show the primer in the upper sequence and the template sequence in the lower sequence, and this indication is different from Schemes 1–3 (the primer in the lower sequence and the template in the upper sequence).
(F) The kit for detecting a polynucleotide according to the present invention The above-described elements necessary for the present invention can be provided in the form of previously combined reagents. Hereinafter, the kit of the present invention is illustrated. The following reagents may be combined with arbitrary components such as those required for label detection, buffer reagents for the reaction solution, or components for positive or negative controls, etc.

The kit of the present invention is as follows:
1. A nuclease-resistant oligonucleotide primer having a sequence complementary to a part of the target polynucleotide of known nucleotide sequence;
2. A DNA polymerase;
3. At least one kind of deoxynucleoside triphosphate; and
4. A nuclease with the activity of decomposing a double-stranded DNA in the 3'→5' direction.

The kit containing ingredients 1–4 may contain additional reagents which are required for the detection of accumulated compound. In the case of the detection of dXMP, for example, the kit may contain reagents for detection of deoxynucleoside monophosphate.

Examples of reaction reagents are phosphorothioated oligonucleotide as a primer, the Klenow fragment of DNA polymerase I, deoxynucleoside triphosphate (labeled with $^{32}P$), exonuclease III, Tris-HCl buffer, $MgCl_2$, BSA and DTT. It also contains EDTA solution to terminate the reaction. Ion-exchange cellulose (PEI=polyethyleneimine cellulose) for thin layer chromatography and LiCl (developing solvent) are used for detection of dXMP. Otherwise, ATP sulfurylase, adenosine-5'-phosphosulfate, luciferin and luciferase are used for detection of pyrophosphoric acid.

The mechanism and effects of the present invention are summarized in the following.

The oligonucleotide primer in the invention is hybridized specifically with the target nucleotide sequence to permit elongation therefrom by DNA polymerase. Said primer may be made nuclease-resistant when previously synthesized or at the time of analysis by binding a deoxynucleotide derivative (SdXTP etc.) in the polymerizing reaction. Then the oligonucleotide primer allows the addition of deoxynucleoside triphosphate (dXTP) by DNA polymerase and the detachment thereof by nuclease. The reaction occurs repeatedly whereby the product decomposed product by nuclease is accumulated in the reaction system. In this way, the present invention provides a quantitative and highly sensitive system.

Even if the primer is hybridized with a sequence other than the target nucleotide, the subsequent reaction does not proceed where dXTP previously added as the substrate is not complementary to the sequence site adjacent to the primer.

Because the present invention does not require the repeated denaturation procedure of heating DNA, it is not required for the reagents including DNA polymerase to be thermally stable, and no complex temperature control is required. Hence, another advantage lies in that the procedures can be readily automated.

The DNA polymerase in the present invention synthesizes a strand complementary to a partial sequence adjacent to the region which said primer has been hybridized with. In this synthesis, 1 mole of PPi is formed upon the addition reaction of 1 mole of dXTP. PPi can be specifically measured by enzyme reaction, that is, the present invention enables the occurrence of signal simultaneously with the elongation reaction. In another embodiment, the elongated chain cleaved off by nuclease may be detected. The use of DNA polymerase can give nuclease resistance to a nuclease sensitive oligonucleotide in the presence of a deoxynucleotide derivative as the substrate.

In the present invention, the nuclease specifically hydrolyzes the strand elongated from the primer hybridized with the target nucleotide until the decomposition reaches the nuclease-resistance site. No hydrolysis occurs in the absence of the target sequence, and even if the target sequence is present, no hydrolysis occurs in the absence of its hybridization with an oligonucleotide and the subsequent elongation of a complementary strand by DNA polymerase. The decomposition product by nuclease is specific to the target polynucleotide and accumulates in the reaction solution in an increasing amount in an linear relationship to the target polynucleotide content, so that highly accurate analysis is feasible.

Another advantage of the present invention lies in the minimal susceptibility to the influence of contamination because even if a sample solution to be examined is contaminated with a reacted sample solution, the accumulated product therein does not function as the template for another round of amplification, and thus the present method is very advantageous in practice.

In addition, the present invention provides a homogenous system for simple operations. The present invention further provides a reaction system not requiring procedures such as hybridization with an additional probe, separation by electrophoresis, etc., by measuring the PPi formed upon addition of dXTP by DNA polymerase. The specific analysis of PPi by enzyme reaction can be carried out in the reaction solution for elongation and decomposition. This advantage is evident in view of the PCR in which probe hybridization and separation by electrophoresis are required for detection of the amplification product.

Another advantage of the present invention lies in the small amount of the primer required. That is, it is sufficient to add the primer in slightly excess relative to the mole ratio of the target nucleotide because the primer hybridized with the target nucleotide in the first reaction permits repeatedly occurring elongation. This is in contrast to a system such as PCR to which the primer should be added in large excess for compensating for the primer consumed as the amplification product. This applies to deoxynucleoside triphosphate as the substrate. For example, the PCR requires four deoxynucleoside triphosphate (dXTP) corresponding to the elongation. On the other hand, it is sufficient in the present invention to add only one kind of deoxynucleoside triphosphate as the substrate complementary to the nucleotide adjacent to the hybridized region. This leads to the simplification of the constitution of reagents.

In another embodiment, the present invention can be applied to the detection of point mutations if the site and the sequence of the point mutation are previously known. In this application, the primer is hybridized with a target nucleotide sequence adjacent to the known site of point mutation, and if a point mutation is present, strand elongation is prevented because of the absence of the nucleotide substrate complementary to the point mutation.

The present method has many advantages as described, and can provide an effective method in gene analysis.

According to the present invention, there is provided a method of detecting a polynucleotide containing a specific sequence useful for diagnosis of genetic disorders and infectious diseases, as well as a kit for detecting a polynucleotide used for said method.

DESCRIPTION OF THE PREFERRED EMBODIMENTS

Figure 1:
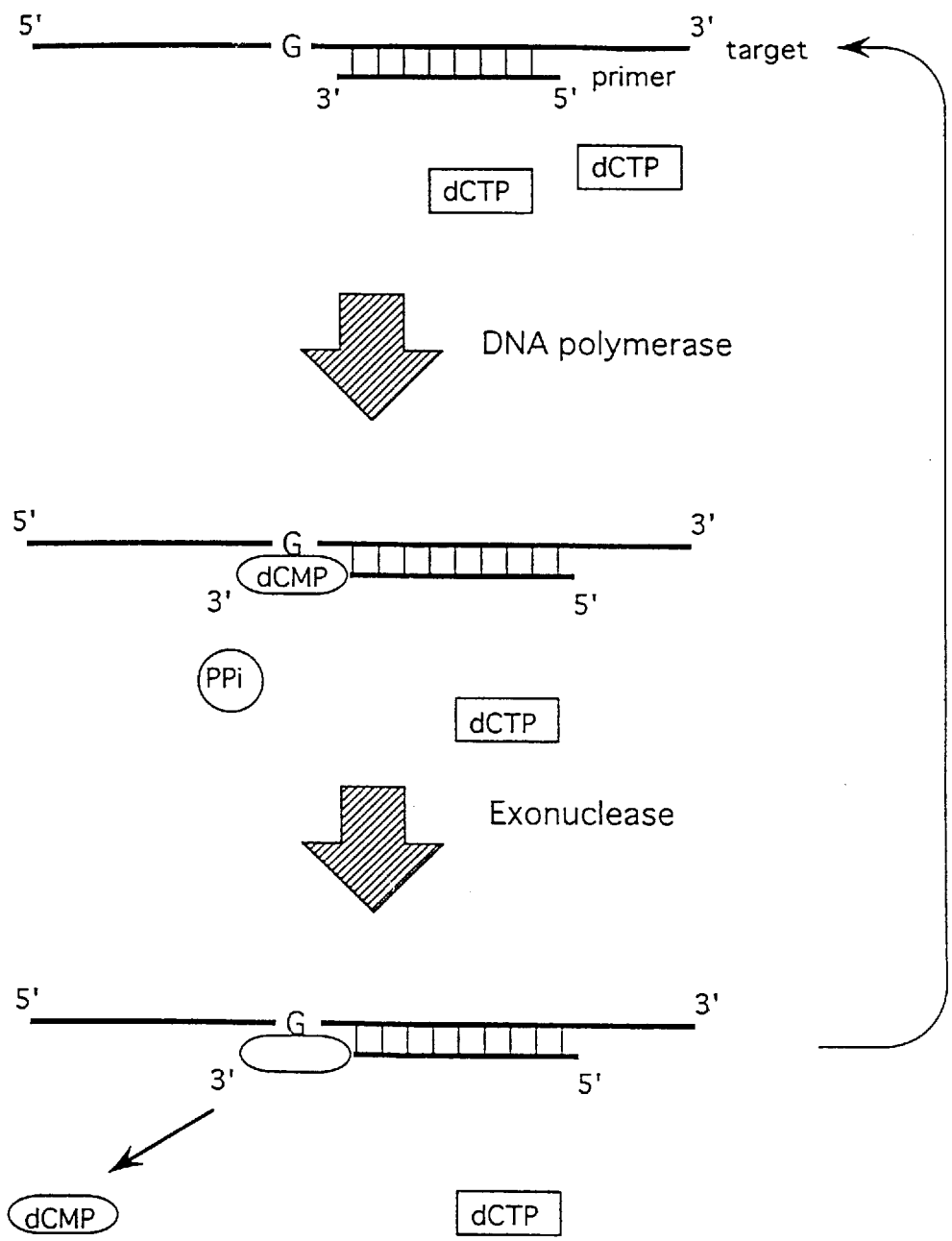
FIG. 1 is a graphic depiction of the reaction principle of the present invention.

Hereinafter, the present invention is described in detail with reference to the following examples, which however should not be construed to limit the scope of the invention.
[EXAMPLE] Detection of a HBV-e antigen gene in HBV-DNA The detection of a HBV-e antigen gene in HBV-DNA was carried out in the following manner. E. Coli -derived exonuclease III (a product of Takara Shuzo Co., Ltd.) was used as the nuclease, and the oligonucleotide of SEQ ID NO 3 was chemically synthesized as the primer DNA.

(1)-1 Preparation of primer DNA

The oligonucleotide of the above sequence (SEQ ID NO 3) was synthesized by the β-cyanoethylamidite method (J. Am. Chem. Soc., 112, 1253–1254 (1990)). A nuclease-resistant oligonucleotide primer was obtained by introduction of a phosphorothioate bond between the T-C at the 3'-terminal using 3H-1,2-benzodithiole-3-one 1,1-dioxide (Beaucage's Reagent) as the reagent for phosphorothioation. A Cyclone® Plus DNA/RNA synthesizer (Japan Millipore Limited) was used for synthesis of the DNA. The synthesized phosphorothioated oligonucleotide was purified in a usual manner by HPLC.

(1)-2 Detection of nucleotide sequence

The oligonucleotide primer was mixed with M13 phage DNA carrying the HBV-DNA as a target nucleotide, and they were subjected to the reaction of the present invention. The composition of the reaction solution is shown below where the final concentrations are indicated. To confirm the progress of the reaction, the reaction was allowed to proceed in the absence of each component. To confirm the necessity of the nuclease-resistant primer in the system, the nuclease-resistant primer was compared with the nuclease-sensitive one carring the same sequence.

When the primer used in this example is hybridized with the target polynucleotide, the nucleotide adjacent to the 3'-terminal is G, so dCTP is required for the synthesis of the complementary strand. The dCTP is then digested by nuclease to give dCMP.

<Compositions>

First reaction solution (5 µl)
  10 fmol target nucleotide (single-stranded DNA with the HBV-e antigen gene on M13 phage DNA)
  1 pmol primer DNA
  50 mM Tris-HCl, pH 7.5
  10 mM $MgCl_2$ Second reaction solution (10 µl)
  1 unit of the Klenow fragment of DNA polymerase I
  5 units of exonuclease III
  10 µM dCTP (labeled with $^{32}P$, $5\times10^4$ cpm)
  50 µg/ml bovine serum albumin (BSA)
  10 mM dithiothreitol In the first reaction, the reaction solution (5 µl) was heated at 100° C. for 5 min. whereby the DNA was made single-stranded. The oligonucleotide primer was then hybridized with the target nucleotide by allowing it to stand at 65° C. for 10 min. The second reaction solution was added thereto and allowed to react at 37° C. for 1 hour. The reaction was terminated by addition of 1 µl of 20 mM EDTA. The whole of the reaction solution was developed by thin layer chromatography (thin layer: PEI-Cellulose F, a product of Merck) at room temperature for 40 min. with 0.4M LiCl as the developing solvent. Then dCMP was detected by autoradiography as the decomposed product by nuclease.

Figure 2:
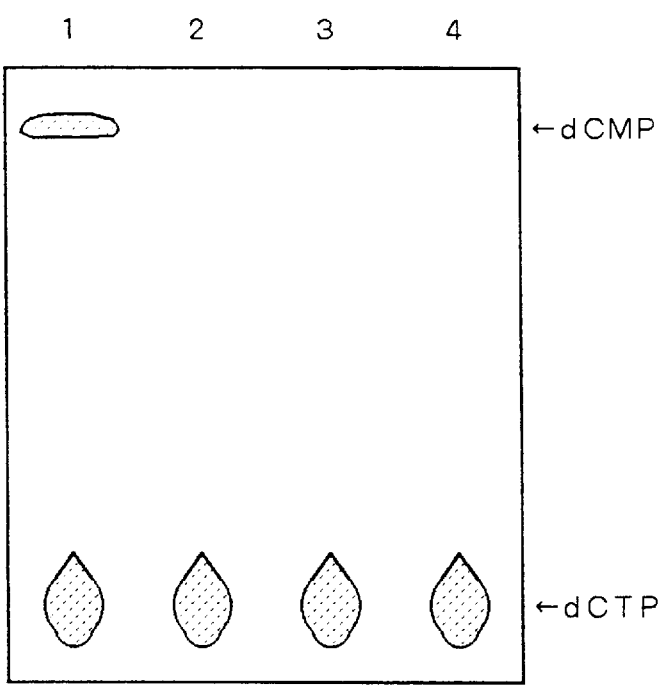
FIG. 2 shows the result of autoradiography of the detection of HBV-e antigen gene according to the present invention.

As is evident from FIG. 2, dCMP as the decomposed product was not detected in the absence of any of the elements, i.e. the target nucleotide, the Klenow fragment and exonuclease III (lanes 2–4), while the reaction according to the present invention proceeded specifically (lane 1). Lane 1 is the system of the present invention (the target nucleotide+ all the reagents), and lanes 2–4 are the same as lane 1 except for the target nucleotide, the Klenow fragment, and exonuclease III are absent in lanes 2–4, respectively.

Figure 3:
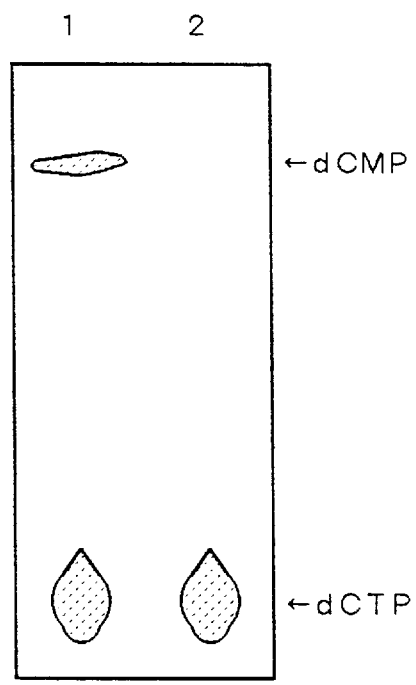
FIG. 3 shows the result of autoradiography in which the accumulation of the decomposition product by the nuclease-resistant primer is compared with that by the nuclease-sensitive one in the system of the present invention.

If the nuclease-sensitive primer is used in instead of nuclease-resistant primer, dCMP as the decomposition product does not accumulate in the reaction system as shown in FIG. 3 (lane 1: nuclease-resistant primer, lane 2: unmodified (i.e. nuclease-sensitive) primer). It is assumed that this result is based on the decomposition of the 3'-terminal region (i.e. the addition site of dCTP) of the primer by nuclease.

(2) Template specificity

It was confirmed in the following experiment that, only where the primer is complementary to the target nucleotide, the substrate (dXTP) is decomposed by nuclease. The reaction conditions were the same as in (1) above except that a primer sequence without any complementary to the target nucleotide (lane 2) and no target sequence was added (lane 3).

Figure 4:
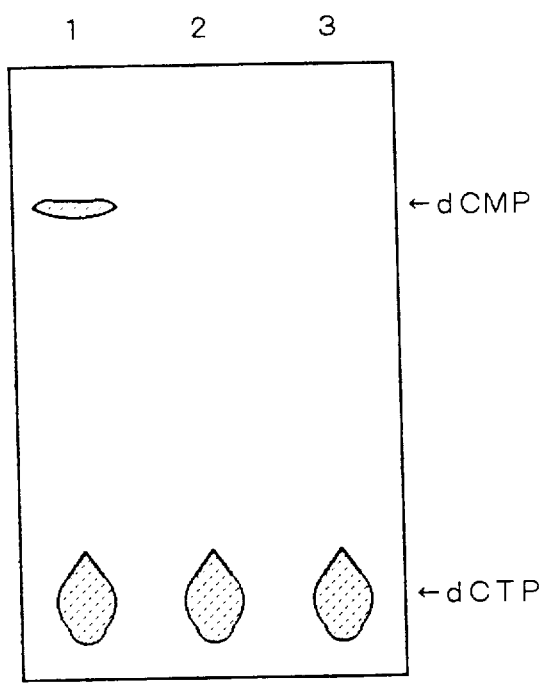
FIG. 4 shows the result of autoradiography of the effect of the complementarity between a primer sequence and its target nucleotide sequence on the accumulation of the decomposition product.

As shown in FIG. 4, dCMP was accumulated as a result of decomposition (lane 1: the target nucleotide complementary to the primer nucleotide), whereas none of the decomposed product was accumulated (lane 2: the target nucleotide identical with (i.e., not complementary to) the primer sequence, lane 3: no target nucleotide). This result indicates that only where the target nucleotide possesses a sequence complementary to the primer does, the reaction of the present invention proceed.

(3) Substrate (deoxynucleoside triphosphate) specificity

The following experiment showed that in a reaction when only dCTP was used as a sole source of deoxynucleoside triphosphate, the substrate is able to be incorporated into the 3'-terminal of the primer. On the contrary, when another kind of deoxynucleoside triphosphate was used as a substrate (dGTP was used in instead of the substrate dCTP in (1) above), decomposed product was not detected.

Figure 5:
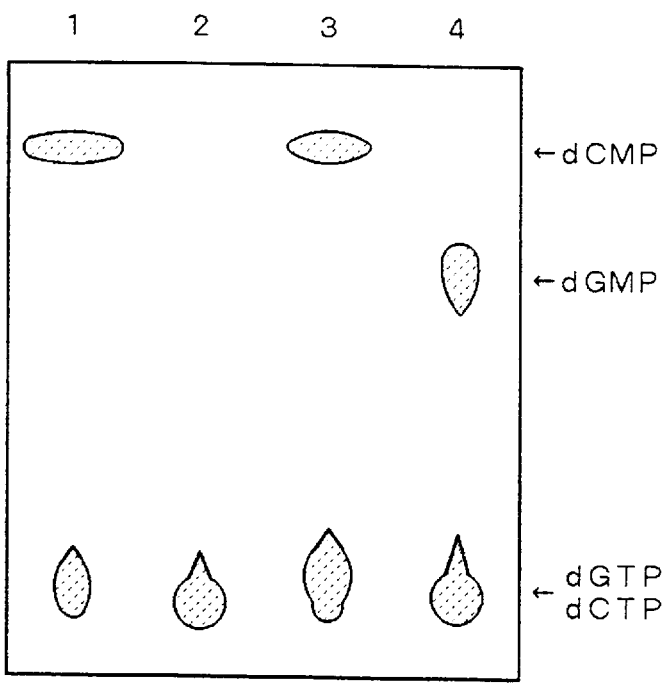
FIG. 5 shows the result of autoradiography in which the accumulation of the decomposition product is examined in the presence of a different kind of substrate.

As shown in FIG. 5 (lane 1: dCTP as a sole source of substrate, lane 2: dGTP as a sole source substrate, lane 3: dCMP and dCTP as markers, and lane 4: dGMP and dGTP as markers), the reaction proceeds only in the presence of dCTP as a sole source of substrate, and the decomposed product (dCMP) was observed (lane 1), whereas no accumulation (i.e. no product formation) occurs in the presence of dGTP as a sole source of substrate (lane 2).

This result indicates that the present method can be applied to the detection of point mutation.

(4) Sensitivity of the present method

Figure 6:
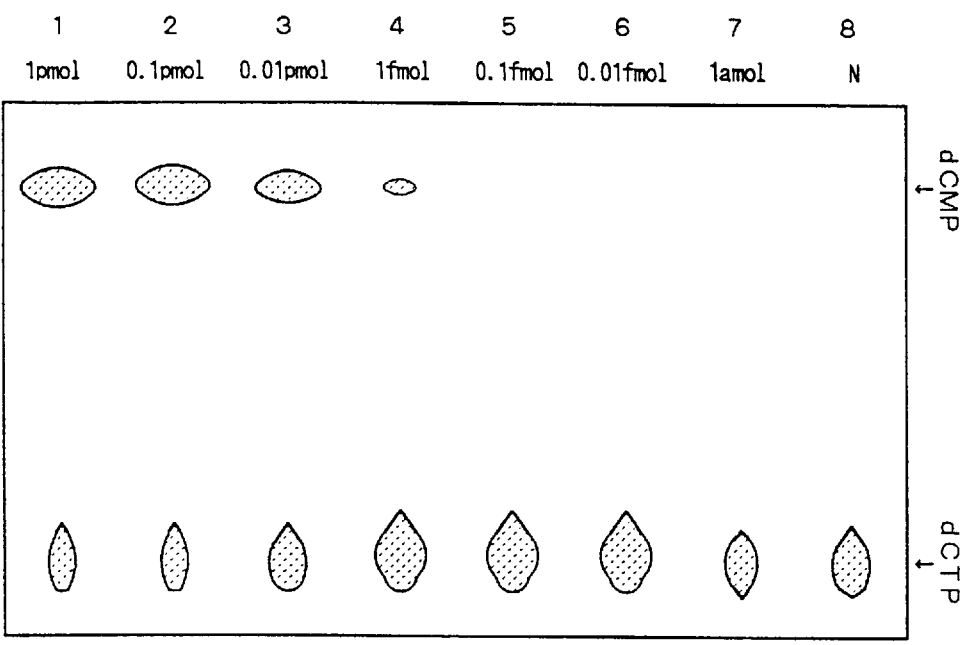
FIG. 6 shows the result of autoradiography of the sensitivity of the present method with a varying concentration of the target polynucleotide.

The sensitivity of the present method was examined on 0 to 1 pmol DNA per reaction mixture as a target nucleotide in the same manner as in (1) above (FIG. 6 and Table 1). 1 fmol DNA (lane 4) could be detected as shown in FIG. 6 (lane 1: 1 pmol of the DNA, lane 2: 0.1 pmol of the DNA, lane 3: 0.01 pmol of the DNA, lane 4: 1 fmol of the DNA, lane 5: 0.1 fmol of the DNA, lane 6: 0.01 fmol of the DNA, lane 7: 1 amol of the DNA, lane 8: no DNA). Thus, the extremely high sensitivity of the present invention was confirmed. Each band was cut off and measured for its radioactivity in a liquid scintillation counter. The results are shown in Table 1. In Table 1, (A) and (B) indicate the radioactivity of each spot (CPM; count per minute). It was confirmed that the sample can be quantitatively determined in the range of 0.1 fmol to 0.01 pmol.

In this example, $^{32}$P-labeled dCTP was previously diluted with unlabeled dCTP in order to visualize a spot clearly in autoradiography. Hence, higher sensitivity can be realized with a higher proportion of labeled dCTP.

TABLE 1

SENSITIVITY OF THE PRESENT DETECTION METHOD

| amount of target DNA | (A) dCTP | (B) dCMP | A − B/Total (%) | dCMP (pmol) | accumulation (dCMP/Target DNA) |
|---|---|---|---|---|---|
| 1 pmol | 6566 | 17883 | 70.9 | 70.9 | 70.9 |
| 0.1 pmol | 8805 | 25024 | 72.5 | 72.5 | 725 |
| 0.01 pmol | 18381 | 15212 | 43.7 | 43.7 | 4370 |
| 1 fmol | 32552 | 1808 | 3.67 | 3.67 | 3670 |
| 0.1 fmol | 31550 | 681 | 0.42 | 0.42 | 4200 |
| none | 35997 | 547 | — | — | |

(5) The present method using T4 DNA polymerase

The present method of detecting the target nucleotide sequence was carried out in the same manner in (1) above except that T4 DNA polymerase was used instead of the Klenow fragment. As described above, T4 DNA polymerase possesses a strong 3'→5' exonuclease activity besides its polymerase activity, so it can be used to eliminate the use of exonuclease in the reaction system.

Figure 7:
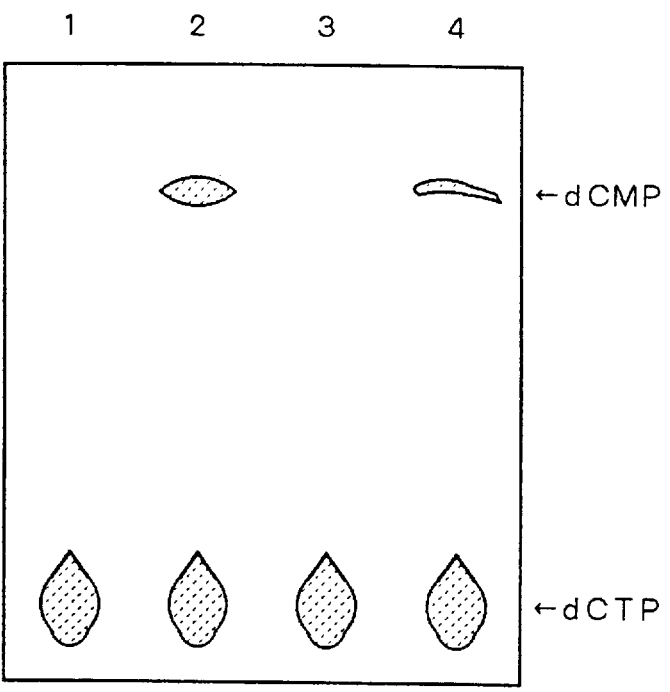
FIG. 7 shows the result of autoradiography in which T4 DNA polymerase is used in the system of the present invention in the absence of nuclease.

4 units of T4 DNA polymerase were used in the reaction system described below. Other reaction conditions were the same as in (1) above. The results are as shown in FIG. 7 (lane 1: Klenow fragment +exonuclease, lane 2: Klenow fragment+exonuclease+target nucleotide, lane 3: T4 DNA polymerase, lane 4: T4 DNA polymerase+target nucleotide). Although the resulting spot (lane 4) was small as compared with the control (lane 2), the formation of dCMP as the decomposed product was confirmed. This result indicates that the reaction according to the present invention can proceed by T4 DNA polymerase in the absence of a nuclease.

<Compositions>

First reaction solution (5 μl)
  10 fmol target nucleotide
  1 pmol primer DNA
  67 mM Tris-HCl, pH 8.8
  6.7 mM MgCl$_2$
  16.7 mM (NH$_4$)$_2$SO$_4$
  6.7 mM EDTA Second reaction solution (10 μl)
  10 mM β-mercaptoethanol
  10 μM dCTP (labeled with $^{32}$P, 5×10$^4$ cpm)
  50 g/ml BSA
  4 units of T4 DNA polymerase (a product of Takara Shuzo Co., Ltd.)

SEQUENCE LISTING

SEQ ID NO: 1
  SEQUENCE LENGTH: 25
  SEQUENCE TYPE: nucleic acid
  STRANDEDNESS: single
  TOPOLOGY: linear
  MOLECULE TYPE: Other nucleic acid Synthetic DNA
  ORIGINAL SOURCE
    ORGANISM: cytomegalovirus (CMV)
  SEQUENCE DESCRIPTION
    CCCCGAAATG GGACCCAGTA CGGAT SEQ ID NO: 2
  SEQUENCE LENGTH: 24
  SEQUENCE TYPE: nucleic acid
  STRANDEDNESS: single
  TOPOLOGY: linear
  MOLECULE TYPE: Other nucleic acid Synthetic DNA
  ORIGINAL SOURCE
    ORGANISM: human oncogene Ki-ras/12
  SEQUENCE DESCRIPTION
    ATAAACTTGT GGTAGTTGGA GCTG SEQ ID NO: 3
  SEQUENCE LENGTH: 25
  SEQUENCE TYPE: nucleic acid
  STRANDEDNESS: single
  TOPOLOGY: linear
  MOLECULE TYPE: Other nucleic acid Synthetic DNA
  ORIGINAL SOURCE
    ORGANISM: HBV-e antigen gene in HBV-DNA
  SEQUENCE DESCRIPTION
    AATGCCCCTA TCTTATCAAC ACTTC 25

---

What is claimed is:

1. A method of detecting a polynucleotide, comprising:

hybridizing a polynucleotide of known nucleotide sequence with a nuclease-resistant oligonucleotide primer having a sequence complementary to a part of said polynucleotide;

then adding a deoxynucleoside triphosphate necessary for elongating the 3'-terminal, DNA polymerase and nuclease thereto, wherein said nuclease is exonuclease III, and said deoxynucleoside triphosphate, said DNA polymerase and said nuclease are present simultaneously with said polynucleotide;

elongating the 3'-terminal of said primer by a base complementary to the corresponding base in said polynucleotide, followed by removal of a base therefrom, wherein the elongation and base removal are repeated one or more times; and detecting the resulting pyrophosphoric acid or deoxynucleoside monophosphate.

2. A method of detecting a polynucleotide according to claim 1, wherein the oligonucleotide primer is phosphorothioated at the 3'-terminal.

3. A method of detecting a polynucleotide according to claim 1, wherein the DNA polymerase is selected from the group consisting of DNA polymerase I, the Klenow fragment of DNA polymerase I, T4 DNA polymerase, T7 DNA polymerase and Phi29 DNA polymerase.

4. A method of detecting a polynucleotide according to claim 1, wherein an atom or a molecule other than phosphoric acid molecules at the $\beta$- and $\gamma$-positions of deoxynucleoside triphosphate is labeled with a radioisotope, and the deoxynucleoside monophosphate formed by nuclease reaction is detected.

5. A method of detecting a polynucleotide according to claim 1, wherein the deoxynucleoside monophosphate formed by nuclease reaction is separated by chromatography and optically measured.

6. A method of detecting a polynucleotide according to claim 1, wherein the pyrophosphoric acid which is formed upon incorporation of a complementary base by DNA polymerase is allowed to react with adenosine-5'-phosphosulfate and adenosine triphosphate sulfurylase to form adenosine triphosphate which is then detected.

7. A method of detecting a polynucleotide according to claim 6, wherein adenosine triphosphate is measured by luciferin-luciferase reaction.

* * * * *

UNITED STATES PATENT AND TRADEMARK OFFICE
CERTIFICATE OF CORRECTION

PATENT NO. : 5,849,487
DATED : December 15, 1998
INVENTOR(S) : TETSU HASE ET AL.

It is certified that error appears in the above-indentified patent and that said Letters Patent is hereby corrected as shown below:

On the title page, item
[54] TITLE

"NUCLEASE RESISTANT" should read --NUCLEASE-RESISTANT--.

COLUMN 1

Line 4, "NUCLEASE RESISTANT" should read
      --NUCLEASE-RESISTANT--.
    Line 8, "1994now" should read --1994, now--.
    Line 38, "e.g." should read --e.g.,--.

COLUMN 2

Line 30, "turn over" should read --turnover--.
    Line 45, "turn over" should read --turnover--.
    Line 57, "turn over" should read --turnover--.

COLUMN 5

Line 8, "the" should be deleted.

COLUMN 8

Line 30, "GTA-" should read --GTAA---.
    Line 39, "GTA-" should read --GTAA---.
    Line 45, "a" should read --an--.

UNITED STATES PATENT AND TRADEMARK OFFICE
CERTIFICATE OF CORRECTION

PATENT NO. : 5,849,487
DATED : December 15, 1998
INVENTOR(S) : TETSU HASE ET AL.

It is certified that error appears in the above-indentified patent and that said Letters Patent is hereby corrected as shown below:

COLUMN 9

```
Line 8,  "confirmed" should read --confirmed.--.
Line 14, "GTA-" should read --GTAA---.
Line 23, "GTA-" should read --GTAA---.
```

COLUMN 11

```
Line 20, "(E)." should read --(E)--.
```

COLUMN 12

```
Line 44, "4and" should read --4 and--.
```

COLUMN 15

```
Line 39, "carring" should read --carrying--.
```

COLUMN 16

```
Line 15, "in" should be deleted.
Line 37, "does," should read --does--.
Line 45, "in" should be deleted.
```

UNITED STATES PATENT AND TRADEMARK OFFICE
CERTIFICATE OF CORRECTION

PATENT NO. : 5,849,487
DATED : December 15, 1998
INVENTOR(S) : TETSU HASE ET AL.

It is certified that error appears in the above-indentified patent and that said Letters Patent is hereby corrected as shown below:

COLUMN 18

```
Line 24, "CGGAT" should read --CGGAT 25--.
Line 35, "GCTG" should read --GCTG 24--.
```

Signed and Sealed this

Twenty-sixth Day of October, 1999

Attest:

Q. TODD DICKINSON

*Attesting Officer*  *Acting Commissioner of Patents and Trademarks*

UNITED STATES PATENT AND TRADEMARK OFFICE
CERTIFICATE OF CORRECTION

PATENT NO. : 5,849,487

DATED : December 15, 1998

INVENTOR(S) : Tetsu Hase et al.

It is certified that error appears in the above-identified patent and that said Letters Patent is hereby corrected as shown below:

Column 10, line 39, "techniques" should be --technique--.

Signed and Sealed this

Twenty-ninth Day of February, 2000

Attest:

Q. TODD DICKINSON

Attesting Officer

Commissioner of Patents and Trademarks